United States Patent
Balasubramaniam et al.

(10) Patent No.: US 6,296,385 B1
(45) Date of Patent: Oct. 2, 2001

(54) APPARATUS AND METHOD FOR HIGH TEMPERATURE VISCOSITY AND TEMPERATURE MEASUREMENTS

(75) Inventors: Krishnan Balasubramaniam, Mississippi State, MS (US); Vimal Shah, Houston, TX (US); R. Daniel Costley; Jagdish P. Singh, both of Mississippi State, MS (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 09/075,922

(22) Filed: May 12, 1998

Related U.S. Application Data

(60) Provisional application No. 60/046,262, filed on May 12, 1997.

(51) Int. Cl.[7] .......................... G01K 11/22; G01N 29/18; G01N 29/20
(52) U.S. Cl. .......................... 374/119; 374/142; 374/139; 73/54.02; 73/597
(58) Field of Search ..................................... 374/117, 118, 374/119, 142, 140, 139; 73/54.01, 54.02, 54.23, 54.24, 54.25, 54.38, 54.39, 54.41, 54.42, 54.43, 597, 627, 629, 630, 631, 644, 617

(56) References Cited

U.S. PATENT DOCUMENTS

| | | | |
|---|---|---|---|
| 2,439,130 | * | 4/1948 | Firestone ................. 374/117 |
| 2,707,391 | * | 5/1955 | McSkimin ............... 73/54.25 |
| 3,062,040 | * | 11/1962 | McKennel et al. ........ 374/119 |
| 3,350,942 | * | 11/1967 | Peltola ..................... 73/597 |
| 3,534,609 | * | 10/1970 | Grenfell et al. .......... 73/597 |
| 3,999,433 | * | 12/1976 | Taplin ..................... 374/117 |
| 4,483,630 | * | 11/1984 | Varela ..................... 374/119 |
| 4,676,663 | * | 6/1987 | Tehon ...................... 374/119 |
| 4,741,200 | * | 5/1988 | Hammerle ............... 73/54.25 |
| 4,762,425 | * | 8/1988 | Shakkottai et al. ....... 374/117 |
| 5,433,112 | * | 7/1995 | Piche et al. .............. 73/54.41 |
| 5,951,163 | * | 9/1999 | Jen et al. .................. 73/597 |

OTHER PUBLICATIONS

Langdon, R.M., "Vibratory Process Control Transducers," Marconi Rev (GB), vol. 43, No. 218 (Third Quarter 1980), pp. 156–175.*

* cited by examiner

Primary Examiner—Diego Gutierrez
Assistant Examiner—Stanley J. Pruchnic, Jr.
(74) Attorney, Agent, or Firm—Piper Marbury Rudnick & Wolfe LLP; Steven B. Kelber

(57) ABSTRACT

A probe for measuring the viscosity and/or temperature of high temperature liquids, such as molten metals, glass and similar materials comprises a rod which is an acoustical waveguide through which a transducer emits an ultrasonic signal through one end of the probe, and which is reflected from (a) a notch or slit or an interface between two materials of the probe and (b) from the other end of the probe which is in contact with the hot liquid or hot melt, and is detected by the same transducer at the signal emission end. To avoid the harmful effects of introducing a thermally conductive heat sink into the melt, the probe is made of relatively thermally insulative (non-heat-conductive) refractory material. The time between signal emission and reflection, and the amplitude of reflections, are compared against calibration curves to obtain temperature and viscosity values.

10 Claims, 11 Drawing Sheets

APPARATUS AND METHOD FOR HIGH TEMPERATURE VISCOSITY AND TEMPERATURE MEASUREMENTS

CROSS-REFERENCE TO RELATED APPLICATIONS

This application is a regular National application claiming priority from Provisional Application, U.S. application Ser. No. 60/046,262 filed May 12, 1997.

This invention was made with U.S. Government support under contract number DE-FG02-93CH0575 awarded by the Department of Energy. The U.S. Government may have certain rights in this invention.

BACKGROUND OF THE INVENTION

1. Field of the Invention

The present invention relates to a method for the non-invasive and simultaneous measurement of viscosity and temperature in very hot liquids (melts) such as polymers, metals, and glass at temperatures ranging from 200° C.–3000° C.

2. Discussion of the Background

Methods for measuring viscosity in liquids are known. Current methods employed for process control, at very high temperatures, infer viscosity from a temperature measurement. This assumes a predetermined relationship between viscosity and temperature. Any slight change in composition, and/or errors in temperature measurement leads to significant errors in viscosity measurement. There are no sensors currently available for measurement of the on-line (in-situ) viscosity measurement for melts at very high temperatures (above 1000° C.). There are no sensors currently available which simultaneously measure temperature and viscosity. However, temperature measurement at high temperature is available using thermocouples. Current methods for measuring temperatures using immersed thermocouples are not desirable due to frequent breakage and inconsistent readings. Moreover, most high temperature applications require probes to be thermally conductive. This leads to a significant heat loss and cooling of molten metal at the probe/melt interface, or in other words, development of a "heat sink."

In view of the aforementioned deficiencies attendant with the prior art methods of measuring the viscosity of very hot liquids, it is clear that there exists a need in the art for an apparatus and method for performing such measurements, which methods avoid a "heat sink."

SUMMARY OF THE INVENTION

Accordingly, one object of this invention is to provide a novel apparatus and method for non-invasively and simultaneously measuring the viscosity and temperature of high temperature molten melts (liquids) while significantly alleviating the heat sink effect of the probe. The probe can be designed to be attached or embedded into one or more of the components which make up the existing melter. The viscosity measurements are made in situ and in "real time", and may be made simultaneously with temperature measurement.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

The present method is a real-time, online and non-invasive method, employing a probe that can range from 0.1–25 inches in length and 0.2–5 inches in width. Online methods for measuring viscosity under these conditions are not currently available. In the present method, the probe is in contact with the hot liquid or melt and real-time viscosity measurements are carried out.

Most high temperature applications require probes to be thermally conductive. This leads to a significant heat loss associated with thermally conductive probes inserted in molten materials at very high temperatures, such as high temperature thermocouples. This not only results in a reduced yield, but can result in eddies and disturbances in the molten flow, reducing quality. The present invention avoids a heat sink by using refractory materials such as high density alumina for the buffer rod material. This permits both temperature and viscosity measurements to be made simultaneously in a very high temperature environment.

Figure 1:
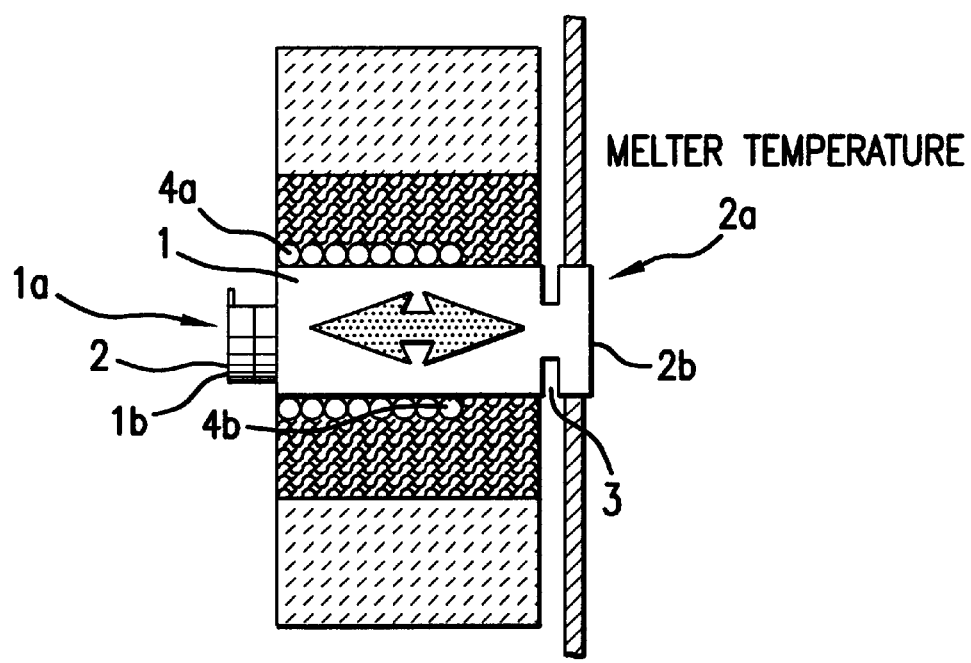
FIG. 1 shows a schematic of the present probe for measuring viscosity of liquids at high temperatures.
Figure 2:
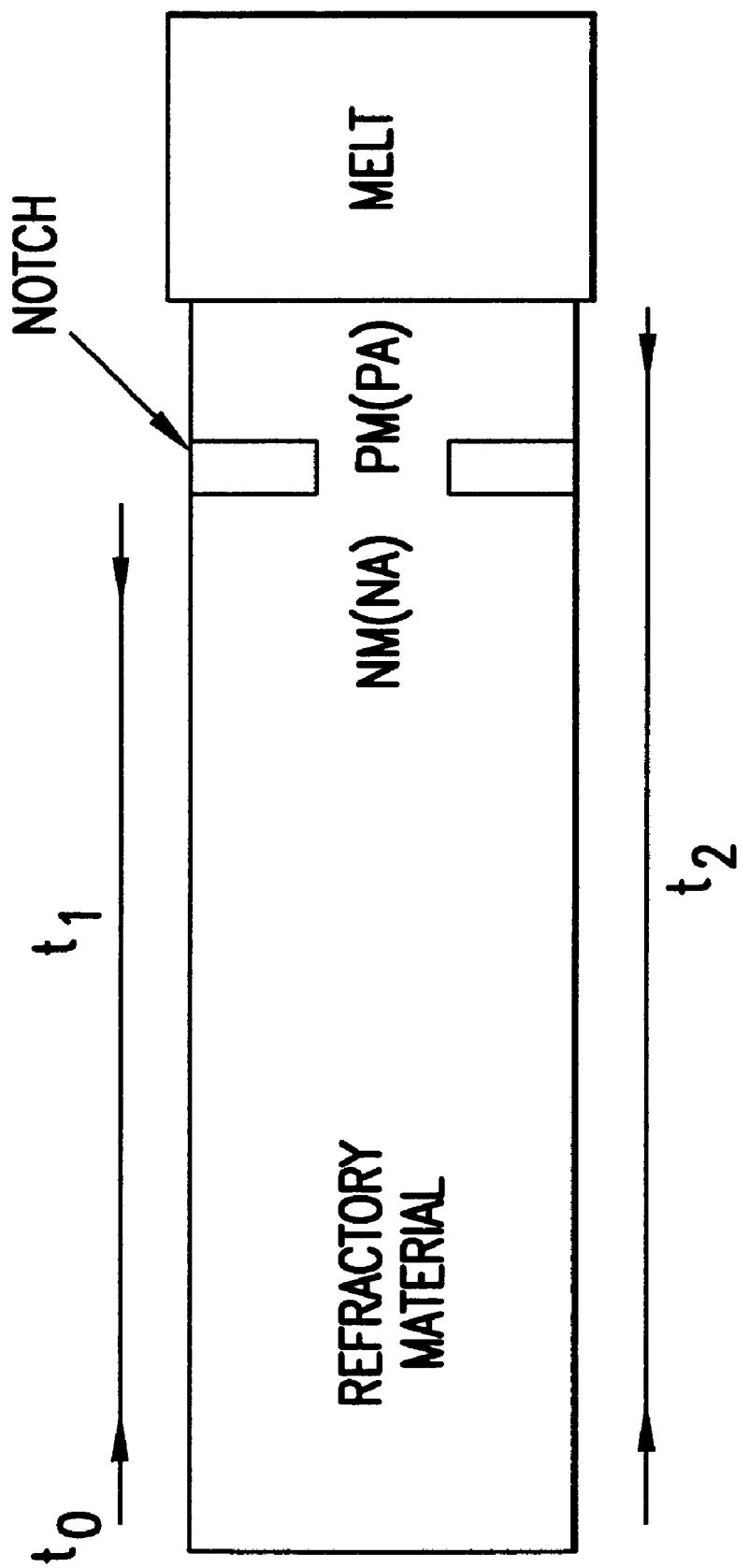
FIG. 2 is a schematic depicting the buffer rod probe of the invention.

The method and apparatus of this invention employs an acoustical waveguide made of an appropriate high temperature resistant (thermally non-conductive) material (such as Alumina, Silicon Carbide, etc.) Referring to FIG. 1, which is a schematic representation of the waveguide, which will be referred to throughout as buffer rod probe 1. The buffer rod probe 1 can be from 0.1 to 25 inches in length, and 0.2 to 5 in width. The first end 1a of the buffer rod probe 1 has piezoelectric shear wave generating transducers/crystals (not shown) bonded to the first end probe surface 1b. The other (second) end 2a is wetted by the viscous liquid (not shown) that is being examined. The first end 1a of the buffer rod probe 1 may be externally cooled (e.g., by a chilling coil having an inlet 4a and outlet 4b, shown in FIG. 6) and thus provides an opportunity to utilize traditional piezoelectric transducers, such as piezoelectric transducer located on the first end 1a. The advantage of this method is the relative cost effectiveness and the simplicity of instrumentation. Shear waves are generated and received by the piezoelectric transducer 2 using a pulser/receiver (not shown). The range of frequency of the piezoelectric transducer 2 is 1–25 MHZ. A circular hairline notch 3 is milled in the buffer rod probe 1 close to the second end probe surface 2a, to provide a constant reference. The notch 3 may be 0.1 inches to just about but not equal to 0.5 times the rod width. Alternatively, a corner reflector (not shown) can be used instead of the notch 3 to provide the reference signal used to measure time difference and viscosity. The two faces (transducer contact surface 1b, and the buffer rod probe surface 2b) as well as the reference notch 3 are precision machined and are parallel. The piezoelectric transducer 2 is connected to instrumentation (not shown) that consists of a pulser to generate the excitation signal. The receiver unit (not shown) gates, filters, amplifies and digitizes the reflected signal from the piezoelectric transducer 2.

Figure 3:
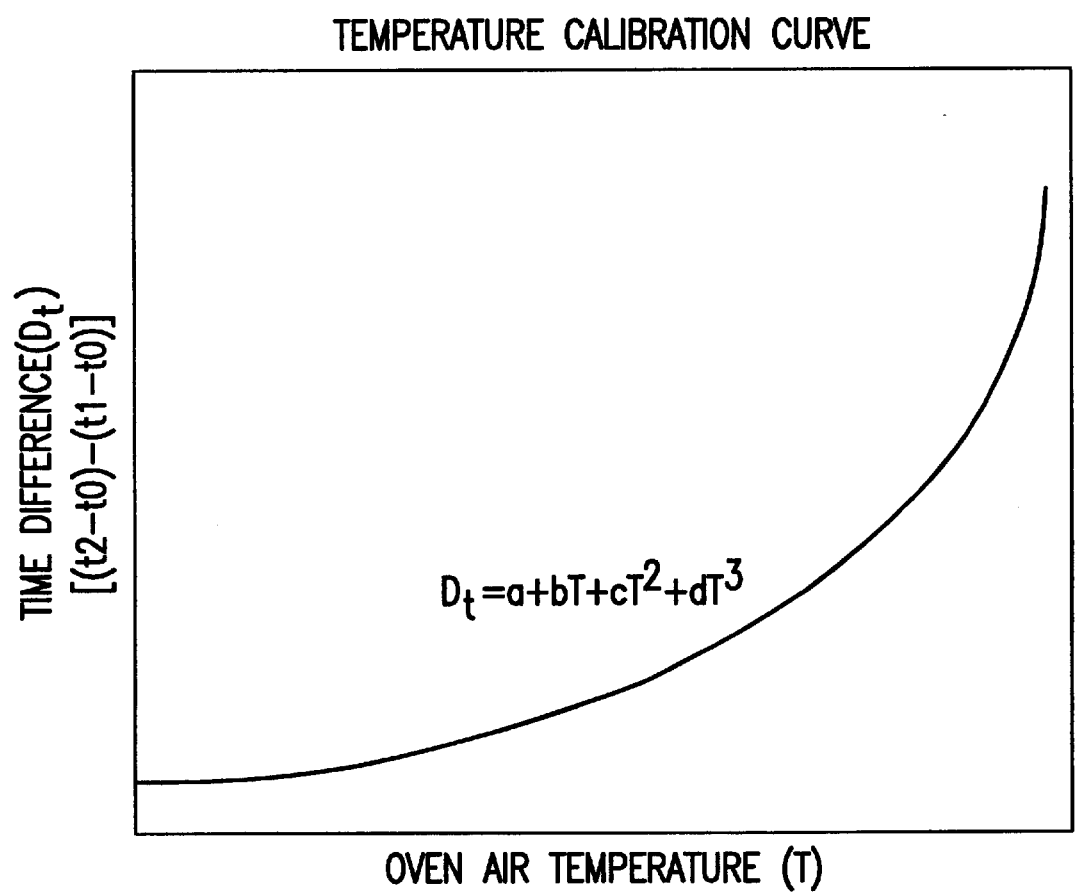
FIG. 3 shows the time difference-oven air temperature relationship for calibrating the probe of the invention.
Figure 4:
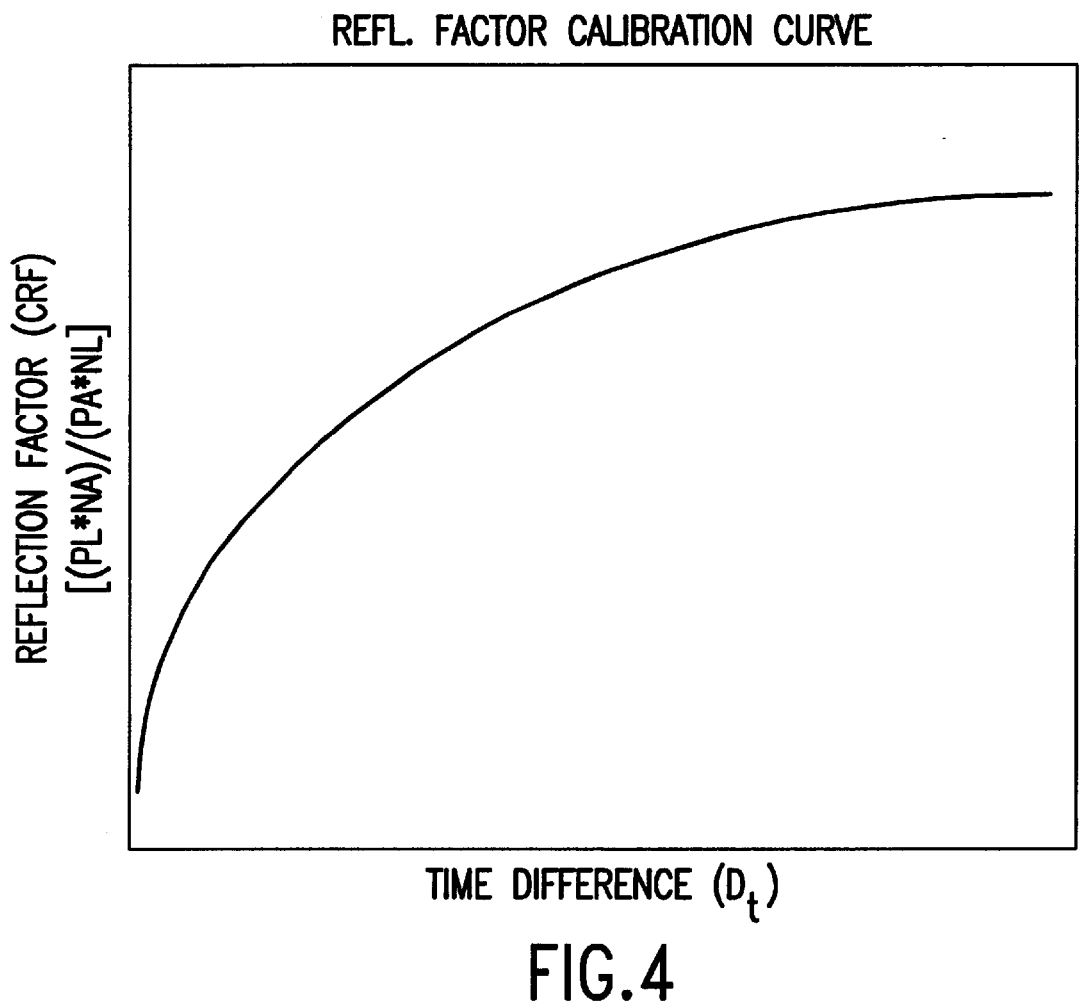
FIG. 4 shows the reflection factor-time difference relationship for calibrating the probe of the invention.

The calibration process involves calibrating the buffer rod probe 1 for the measurement of temperature and viscosity. A typical calibration method consists of the following; in the first step temperature calibration is performed as shown in FIG. 3. The buffer rod probe surface is in contact with air (which is assumed to have zero viscosity from practical aspects). This can be performed in a high temperature oven such as an electrical induction oven with capability to heat up to at least 1600° C. The temperature of air inside the oven is measured using a commercially available calibrated RTD thermocouple. Temperature inside the oven is slowly increased from room temperature to 1600° C. and the echo arrival times in the shear ultrasound transducer are measured. Time taken for the shear ultrasound wave to travel to the notch and back is measured first (t1–t0) and then the probe interface echo is measured (t2–t0). The time difference (DTM) between the arrival of the two echoes is then plotted as a function of the oven air temperature. This graph provides the temperature calibration assuming that the oven air, the notch and the probe interface are all at steady state. The peak-to-peak amplitudes of the reflected echoes from the notch (NA) and the probe interface (PA) in contact with air are also recorded as a function of oven temperature.

The second step # is to calibrate for viscosity. This is accomplished by repeating the above experiment with the probe interface in contact with a calibrated standard such as glass that has a density close to the actual material for which the sensor is being designed. The peak-to-peak amplitudes of the reflected echoes from the notch (NM) and probe surfaces (PM) are measured along with the time difference between the echoes. The calibration reflection factor (CRF) is defined as the ratio (PM*NA)/(NM*PA). The plot between the calibration reflection factor (CRF) and the time difference will provide the reflection factor calibration curve.

Figure 5:
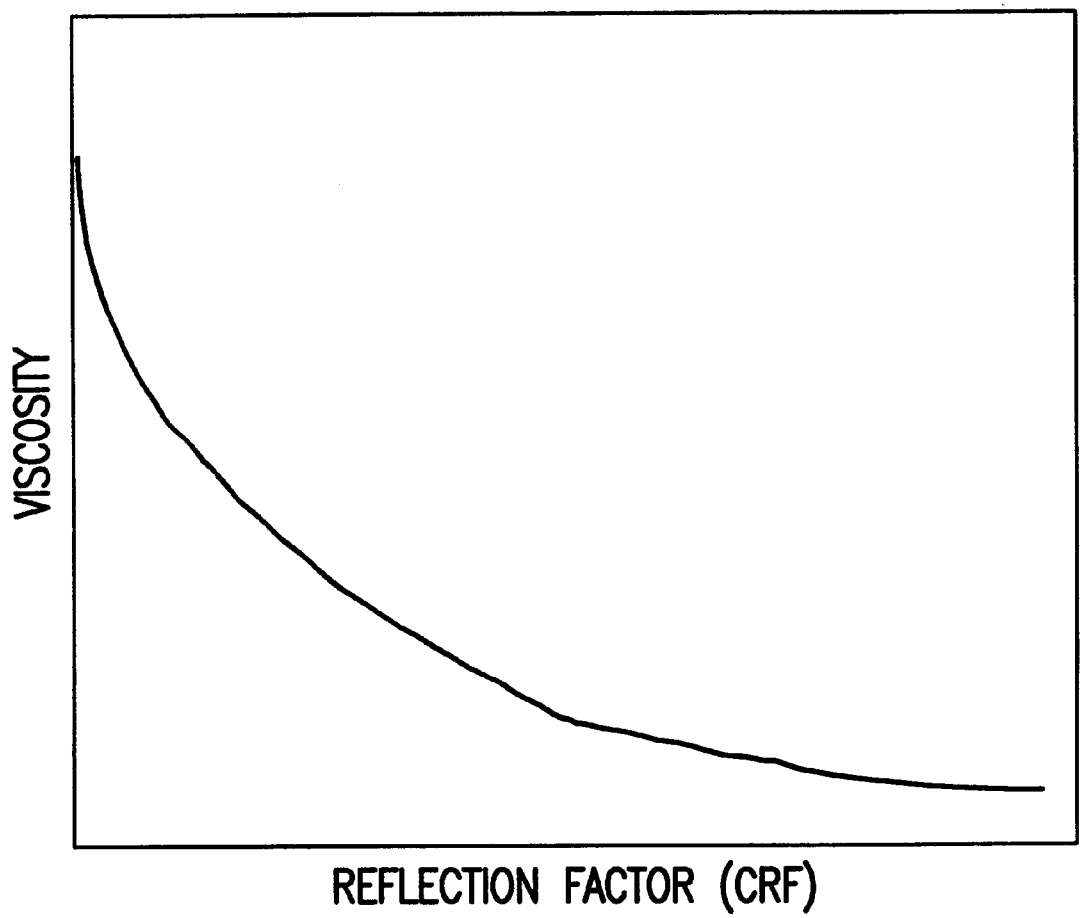
FIG. 5 shows the viscosity-reflection factor relationship for calibrating the probe of the invention.

The third curve uses a pre-calibrated curve between the liquid viscosity and the liquid temperature obtained for the standard (for instance glass) from the manufacturer or through other viscosity testing methods. This curve is used with the reflection factor calibration curve and the temperature calibration curve to obtain the relationship between calibration reflection factor (CRF) and viscosity (V) as shown in the FIG. 5.

Once these three curves are available for a particular geometry and material of the buffer rod, the sensor system can be used to measure viscosity, particularly between the range of 0–30,000 poise at temperatures between 500–1600° C.

The measured quantities during the implementation of the buffer rod are the time difference (DTM) and the reflection amplitudes from the notch and the probe surface (NM and PM). The time difference provides the temperature of the liquid and the reflection factor provides the viscosity measurement. The calibration curves are used for the reconstruction of the viscosity and temperature measurement. The measured reflection factor (MRF) is defined as [PM(DTM) *NA(DTM)]/[NM (DTM)*PA(DTM)], where PA(DTM) and NA(DTM) are obtained from the calibration data set. The MRF is then used to measure viscosity from the viscosity calibration curve shown in FIG. 5.

In one embodiment of the present method of measuring viscosity, multiple reflections from the notch and the probe surface due to reverberation are used to increase sensitivity. In another embodiment, a longitudinal wave is used to account for large variations in the bulk modulus of the liquid.

Having generally described this invention, a further understanding can be obtained by reference to certain specific examples which are provided herein for purposes of illustration only and are not intended to be limiting unless otherwise specified.

Examples 1

Figure 6:
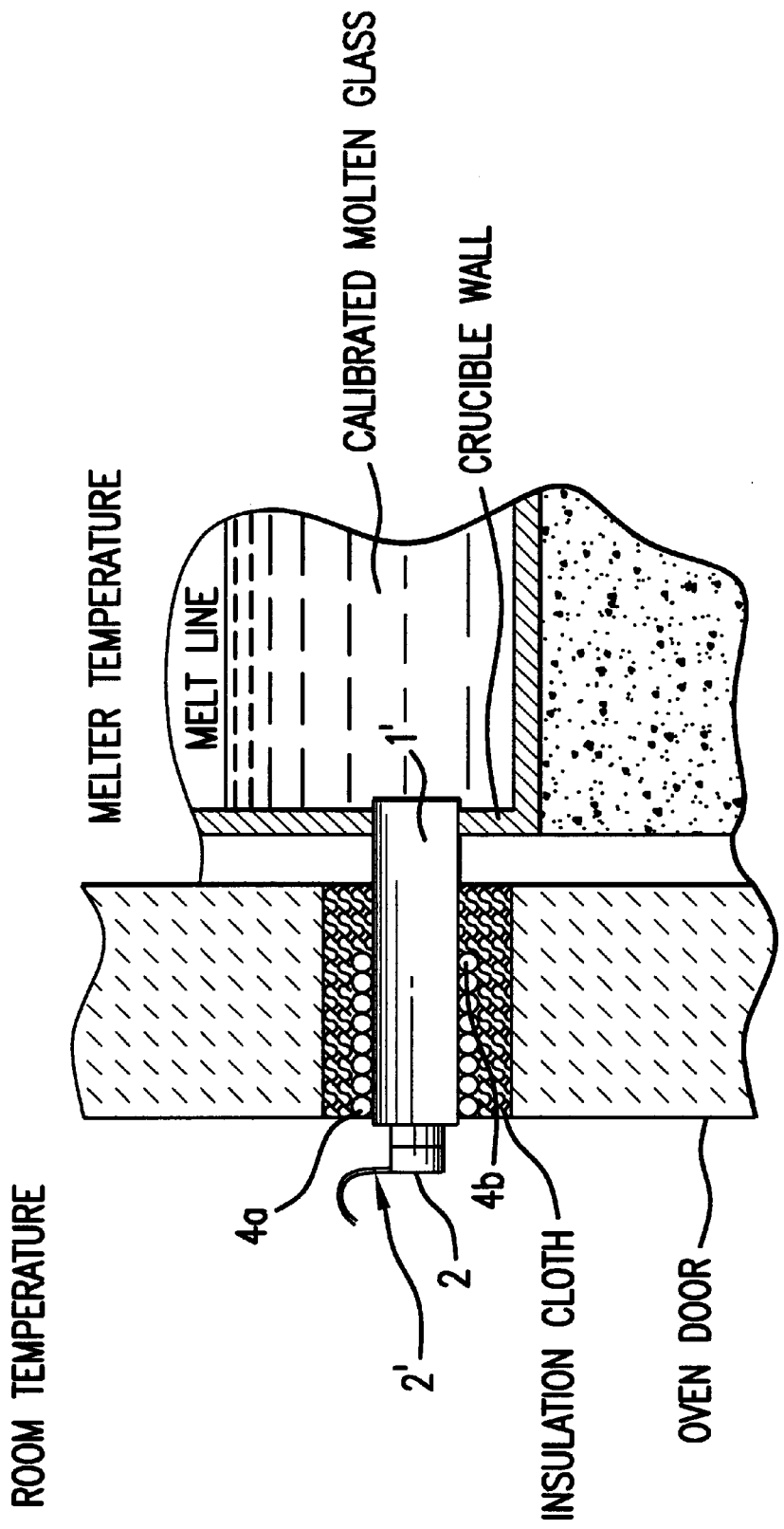
FIG. 6 shows a schematic representation of the experimental verification of the probe.
Figure 7:
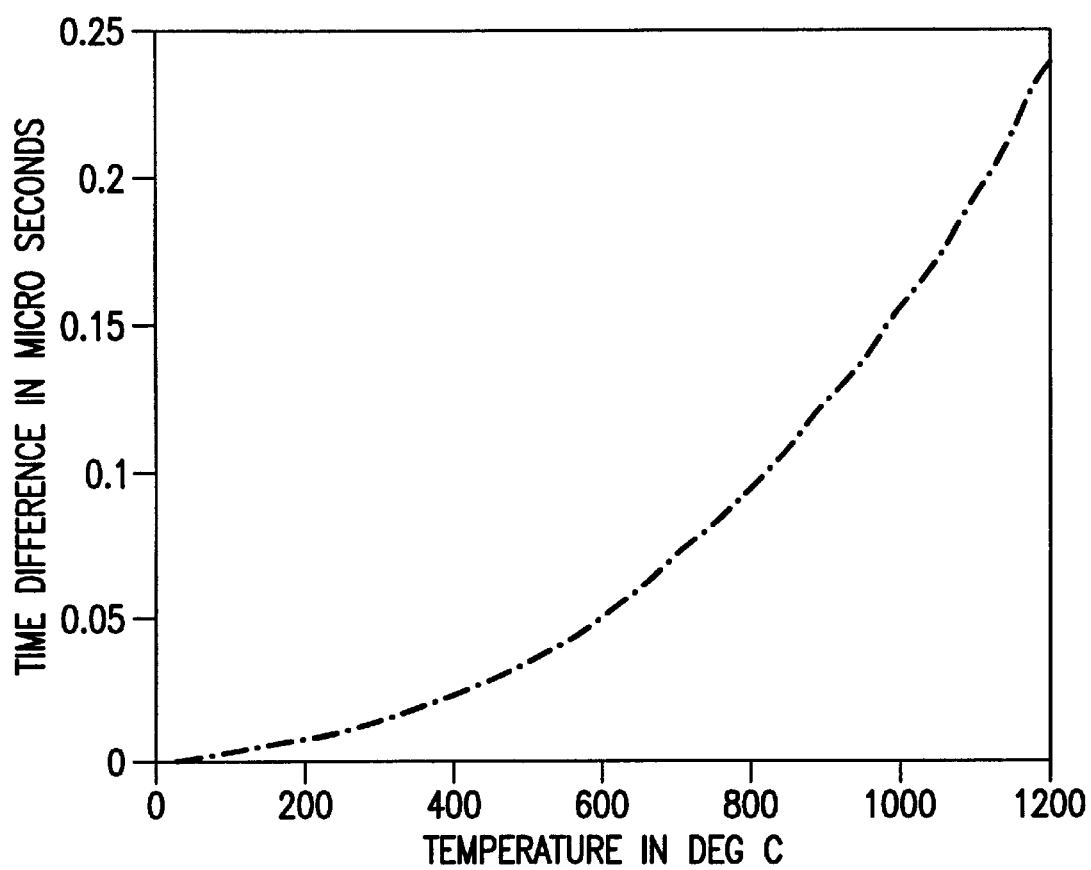
FIG. 7 is a graphical representation of oven temperature versus time difference (DTM).
Figure 8:
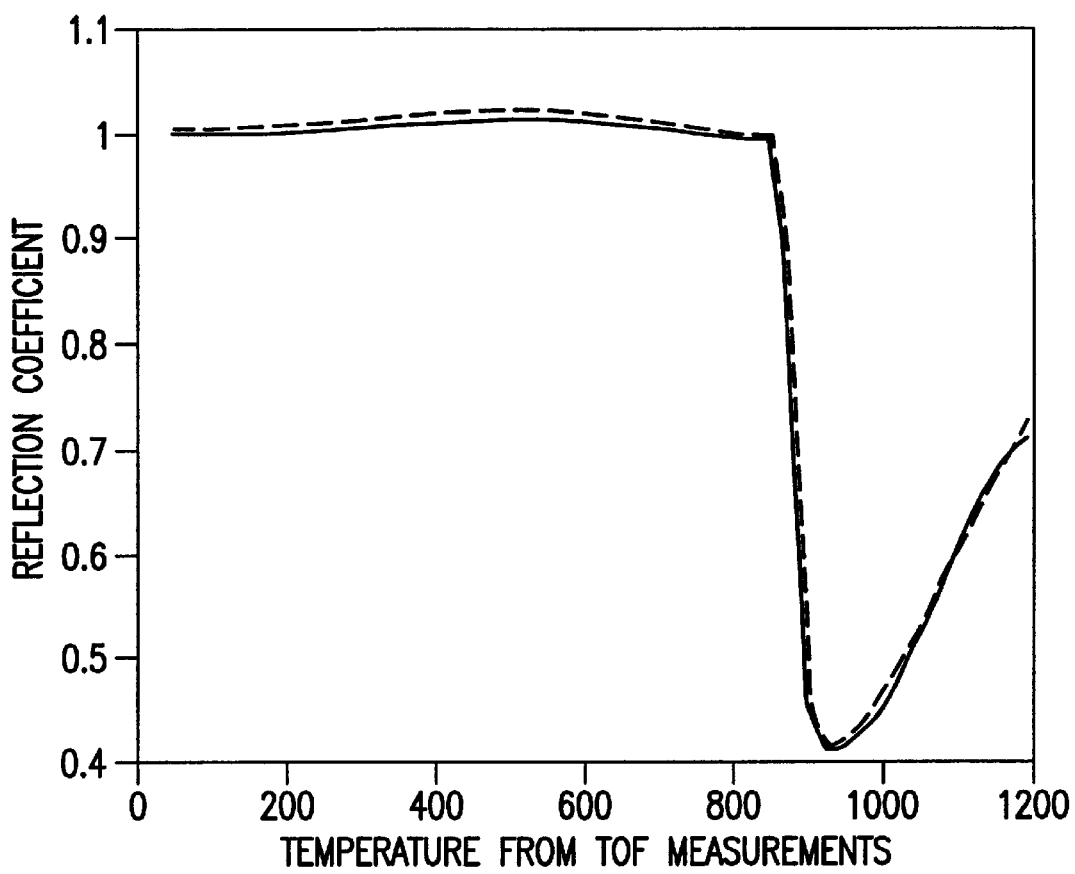
FIG. 8 is a graphical representation of refection factor (MRF) versus oven temperature.

Experiments to evaluate the effects of temperature gradients and the applicability of temperature compensation at very high temperatures were carried out. The experimental set up is shown in FIG. 6 where an alumina "buffer rod" 1' acts as a solid substrate. Since the transducer cannot withstand excessive temperatures, a chilling coil (including an inlet 4a and an outlet 4b) was introduced which would bring down the temperature at transducer contact 2' to room temperature. Other chilling devices, such as a cooling air flow, cooled liquid contact or both, or an appropriate heat sink may be used. The buffer rod was calibrated using an empty crucible to observe the effect of temperature gradients on the ultrasound properties. The results are shown in FIGS. 7 and 8. FIG. 7 illustrates the relationship between the time difference versus temperature calibration curve measured in air. A sample glass obtained from FERRO Corporation, IP745, was introduced into a crucible and heated. In FIG. 8, the data represents reflection factor from the Alumina buffer rod-melt glass which is being heated from room temperature to 1200° C. The Alumina buffer rods were obtained from Coors Ceramics, Denver Colo., and are high grade quality. The shear transducer used was obtained from Krautkramer Branson and was a Y-cut type with broad band specification with central specified frequency of 10 MHZ. The Panametrics 5052PR instrument was used to pulse the transducer, receive and amplify the signal. The Analog-to-Digital conversion was performed using a Tektronix TDS320 digital oscilloscope and the data was transferred to the PC using a IEEE488.2 GPIB interface. The Digital data was then processed and analyzed using MATLAB™ (computer software for matrix calculation) software.

Example 2

Figure 11A:
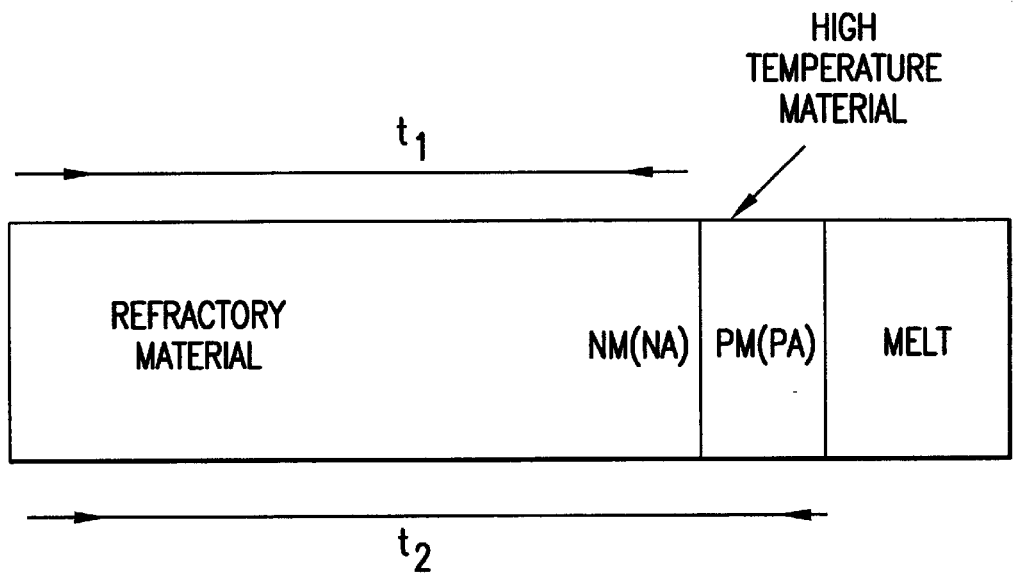
FIG. 11a is a schematic showing the modification of the buffer rod probe using a high temperature layer.
Figure 11B:
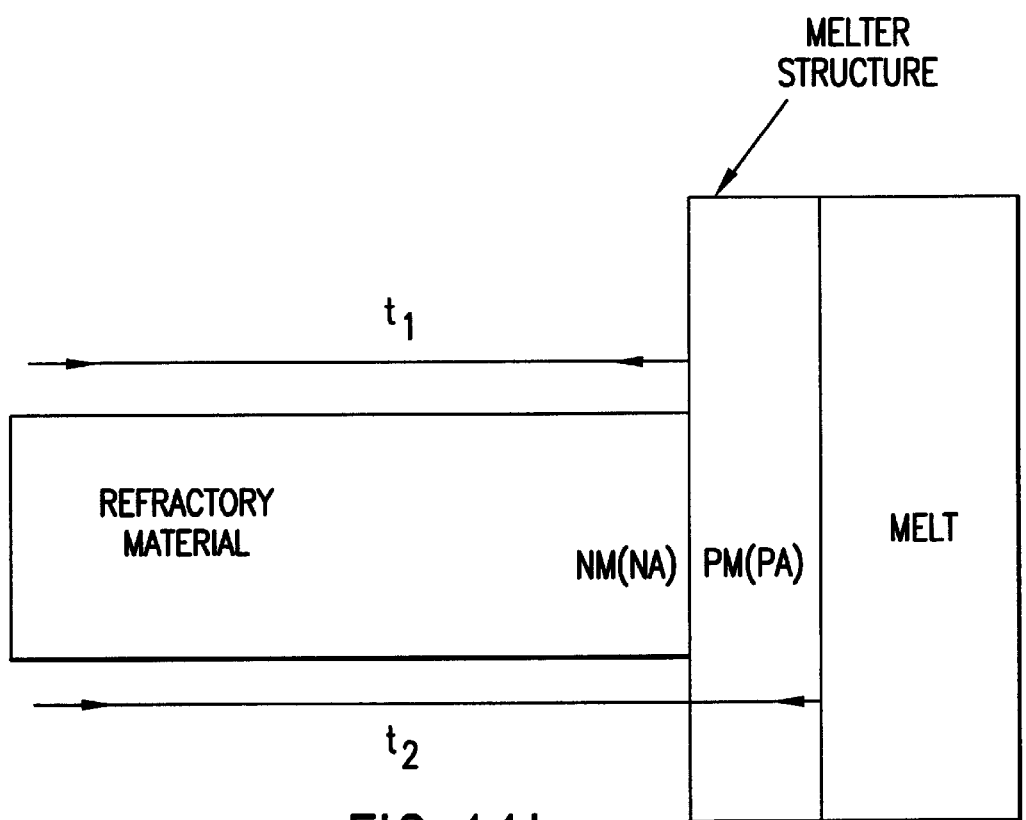
FIG. 11b is a schematic showing the modification of the buffer rod probe using a melter component as a high temperature layer.

Modifications to the buffer rod include using another layer of high temperature material (such as molybdenum, INCONEL™ (nickel alloys and alloys of nickel, chromium and iron), tantalum, etc.). This material is bonded to the parent buffer rod (which does not have a notch or any other form of reference reflector inside). The ultrasonic signal is in part transmitted and in part reflected at the interface between the two materials. The reflection signal from the interface between the two materials is used as reference (NM/NA) (replacing the notch signal). The reflected signal from the interface between the layer material and the fluid is used as the signal from the probe surface (PM/PA) (replacing the probe signal). Another modification is the use of the already existing high temperature material of a component in the melter (such as the wall of the melter, wall of the pour-nozzle, wall of the stop rod, etc.) as the reference media as shown in FIG. 11a. This can be accomplished by bonding the buffer rod (without the notch) on to the melter component and by using the interface between the buffer rod and the melter component as the reference signal for both time and amplitude measurement. A schematic of this is shown in FIG. 11b.

Example 3

Figure 10:
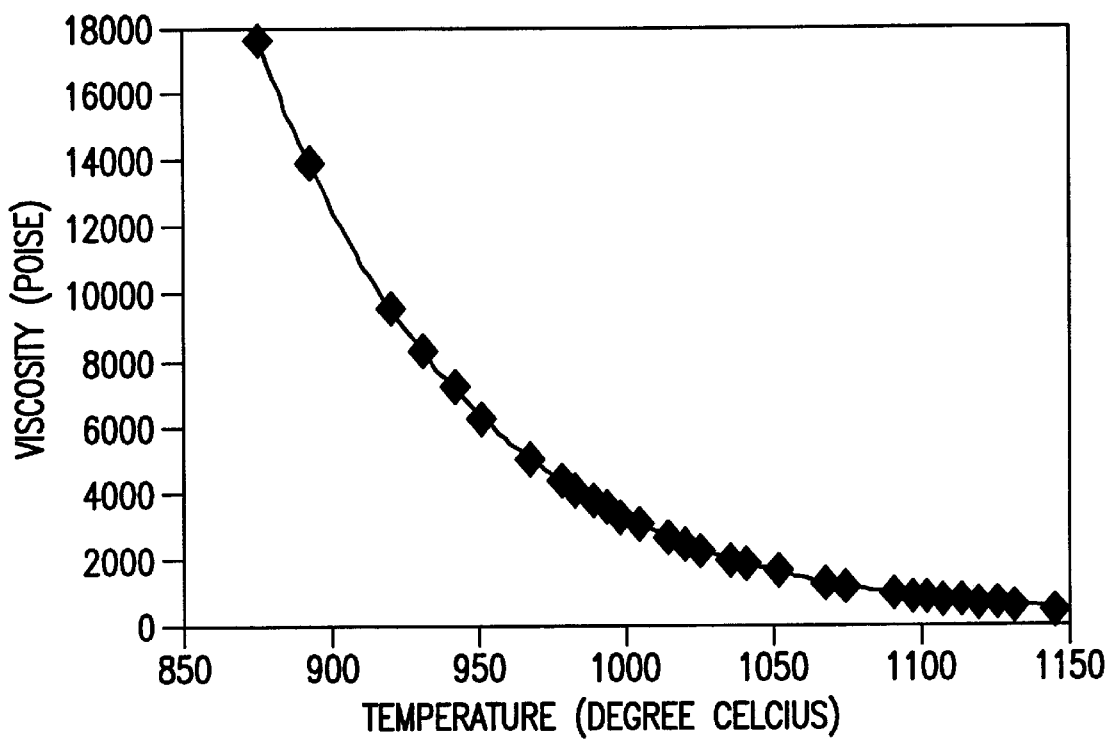
FIG. 10 is a graphical representation of results for measured viscosity of a glass melt using the claimed invention, verses measured temperature for the same melt.

Using the buffer rod of Example 2, the viscosity of a melt prepared from a glass sample obtained from Ferro Corporation of MI, USA was measured. Viscosity was recorded real time and graphed against temperature measured at the same time. The result is reflected in FIG. 10.

Example 4

Figure 9:
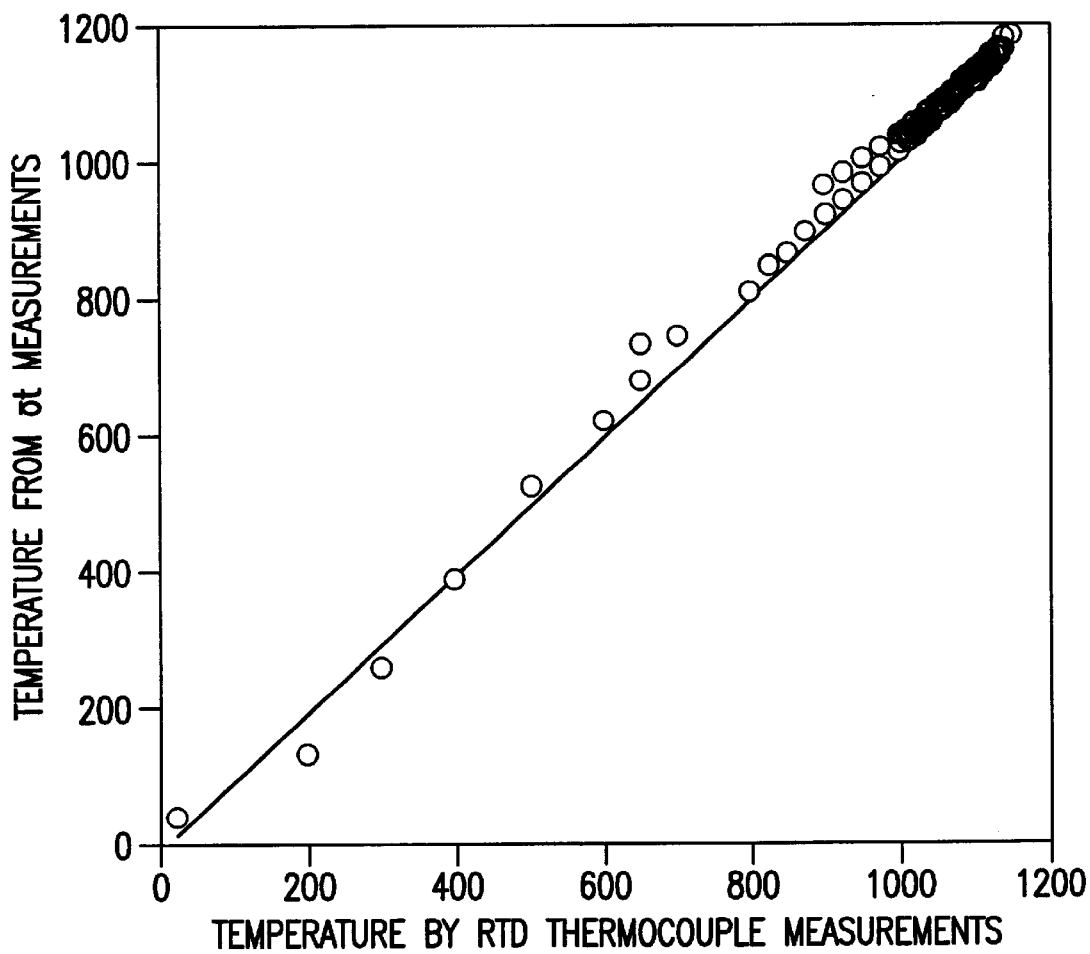
FIG. 9 is a graphical comparison of temperature measurement of a glass melt by RTD thermocouple and by the claimed invention.

Using the buffer rod of Example 2, temperature of a melt during heating and cooling as a glass melt was obtained, and compared with results obtained using an RTD thermocouple. The data is reflected in FIG. 9.

This application is based on U.S. application Ser. No. 60/046,262, filed May 12, 1997, which is incorporated by reference herein in its entirety.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A probe for simultaneously measuring viscosity and temperature of a hot liquid, comprising:
(a) a buffer rod comprising a refractory material acoustical waveguide comprising a first inner refractory material encased in a second outer refractory material, said buffer rod having a first and second end, said second end comprising a buffer rod probe surface, wherein the inner refractory material is a high temperature resistant, reduced heat sink material selected from the group consisting of alumina, silicon carbide and mixtures thereof; and
(b) an ultrasonic shear wave generating transducer at the first end of the buffer rod;
wherein said ultrasonic shear wave generating transducer emits shear waves that are in part transmitted and in part reflected at the interface between the two refractory materials; and
wherein the shear waves reflected at the interface between the two refractory materials provide a reference signal that can be used to measure time differences.

2. The probe of claim 1, wherein said first end is provided with a means for cooling said transducer.

3. The probe of claim 1, wherein the transducer is piezoelectric.

4. The probe of claim 1, wherein said probe measures the temperature and viscosity of said hot liquid at the buffer rod probe surface.

5. The probe of claim 1, wherein said liquids are at a temperature of 500° Celsius to 1600° Celsius.

6. The probe of claim 1, wherein said probe can measure viscosities from 0–2000 poise.

7. The probe of claim 1, wherein said transducer, has a frequency range of from 1–25 MHZ.

8. The probe of claim 1, wherein said buffer rod dimension is 0.1–25 inches long and 0.2–5 inches wide.

9. The probe of claim 1, wherein said outer refractory material is a high temperature material selected from the group consisting of molybdenum, inconel and tantalum.

10. A method for simultaneously determining viscosity and temperature of a molten material, comprising:
(1) inserting the second end of the probe of claim 1 into said molten material;
(2) causing said shear wave generating transducer to emit shear waves through said waveguide to said molten material, wherein said shear waves shear a surface of said molten material and are reflected;
(3) detecting reflections of said shear waves through said transducer, and determining said viscosity and temperature of said molten material by comparing a time difference between said shear waves emission and reflection detection to determine temperature and by comparing amplitude of said reflection to determine viscosity.

* * * * *